United States Patent [19]

Kresch et al.

[11] Patent Number: 5,456,689
[45] Date of Patent: Oct. 10, 1995

[54] METHOD AND DEVICE FOR TISSUE RESECTION

[75] Inventors: Arnold J. Kresch, 4 Horseshoe Bend, Portola Valley, Calif. 94028; Donald L. Alden, Sunnyvale, Calif.

[73] Assignee: Kresch; Arnold J., Portola Valley, Calif.

[21] Appl. No.: 136,426

[22] Filed: Oct. 13, 1993

[51] Int. Cl.⁶ ................................................. A61B 17/32
[52] U.S. Cl. ........................... 606/180; 606/170; 604/22
[58] Field of Search ............................. 604/22; 128/3–6, 128/24 AA, 666.02; 606/159, 170, 171, 180, 39, 40, 45, 46

[56] References Cited

U.S. PATENT DOCUMENTS

| | | |
|---|---|---|
| 2,012,363 | 8/1935 | Vogel . |
| 3,147,749 | 9/1964 | Marsh . |
| 3,942,530 | 3/1976 | Northeved . |
| 4,132,227 | 1/1979 | Ibe . |
| 4,607,621 | 8/1986 | Wheeler . |
| 4,681,106 | 7/1987 | Kensey et al. . |
| 4,756,309 | 7/1988 | Sachse et al. . |
| 4,834,729 | 5/1989 | Sjostrom . |
| 4,842,578 | 6/1989 | Johnson et al. . |
| 4,936,281 | 6/1990 | Stasz . |
| 4,986,825 | 1/1991 | Bays et al. . |
| 4,998,527 | 3/1991 | Meyer . |
| 5,000,185 | 3/1991 | Yock . |
| 5,019,036 | 5/1991 | Stahl . |
| 5,092,872 | 3/1992 | Segalowitz . |
| 5,133,713 | 7/1992 | Huang et al. ........................... 606/180 |
| 5,176,677 | 1/1993 | Wuchinich ............................. 606/171 |
| 5,201,731 | 4/1993 | Hakky . |
| 5,313,949 | 5/1994 | Yock ................................. 128/662.02 |
| 5,314,438 | 5/1994 | Shturman ................................. 606/159 |
| 5,325,860 | 8/1994 | Seward et al. . |
| 5,335,663 | 8/1994 | Oakley et al. . |
| 5,345,940 | 9/1994 | Seward et al. ..................... 128/662.02 |

Primary Examiner—Stephen C. Pellegrino
Assistant Examiner—William Lewis
Attorney, Agent, or Firm—Townsend and Townsend and Crew

[57] ABSTRACT

A tissue resection device for preferred use in an organ inflated with non-conductive optically transparent fluid under pressure is disclosed. The instrument includes a rigid shaft having a proximal end, a distal end, and defining a perfusion lumen extending therebetween. At the distal end of the shaft, the shaft is provided with a rounded blunt end having an elongate aperture exposing the lumen near the distal end. A drive tube is rotatably disposed within the shaft lumen and has a proximal end, a distal end, and a drive tube aspiration lumen extending therebetween. A cutting head is mounted on the distal end of the drive tube and has a laterally disposed cutting edge which can resection either by conventional cutting or electrocautery. This laterally disposed cutting edge is communicated to an internal passage between the cutting edge and the aspiration lumen of the drive tube so that tissue severed as the cutting head is rotated may be drawn directly into the aspiration lumen. A housing attached to the proximal end of the shaft. Preferably, a DC motor in the housing is connected to rotate the drive tube and thus the laterally disposed cutting head. Connection is provided on the housing for connecting the perfusion shaft lumen to a perfusion source and the aspiration lumen to an aspiration source. Preferably, an optic fiber at the proximal end of the elongate aperture of the shaft provides an optical view of surgery while a proximally mounted and laterally exposed ultrasound transducer is disposed with a solid angle of interrogation including the surgical-site.

36 Claims, 10 Drawing Sheets

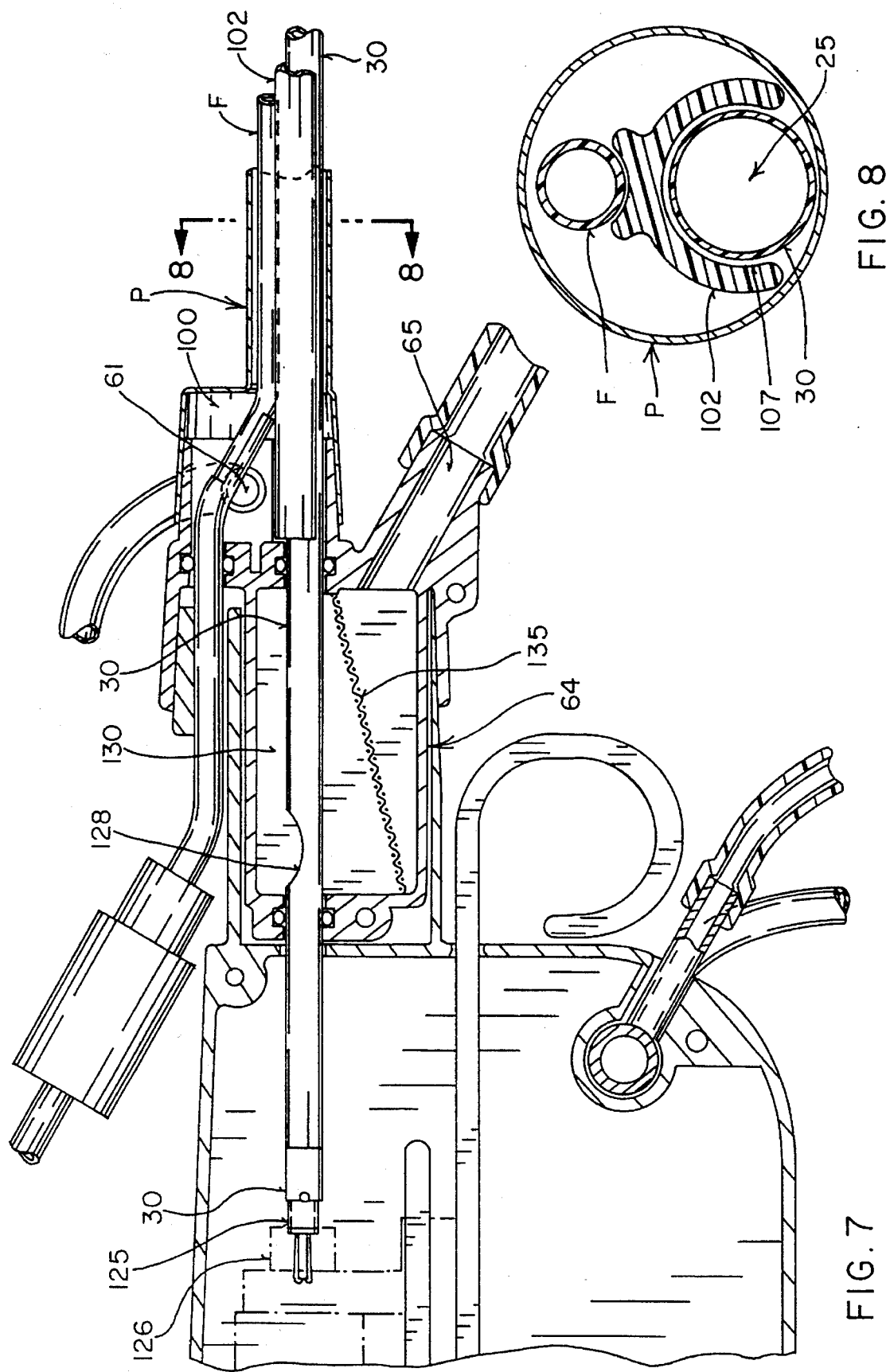

METHOD AND DEVICE FOR TISSUE RESECTION

This invention relates to a method and device for tissue resection, especially surgical treatment of the uterus or prostate.

BACKGROUND OF THE INVENTION

Electrocautery has been in use for many years as a general surgical tool, such as for trans-cervical fibroid removal. The uterus is first flooded under pressure with a non-conductive sorbitol-mannitol fluid under sufficient pressure to separate the walls of the uterus and render the surgical site suitable for optical fiber observation under a procedure generally described as uterine cavity distension. During this flooding, an electrocautery surgical tool is inserted into the uterus through the cervix. Electrical current at high power settings (an alternating current about 750 KHz) is transmitted from the cutting surface of the surgical instrument to the surgical site. The cutting surface usually consists of a wire or solid shape. The transmission of current to the uterus is monopolar and completed by a conductive path to the power unit through a conductive pad applied to the patient's skin.

The electrical current is concentrated at the cutting surface. Heat generated from the resistance of tissue to the flow of electrical current is high enough to vaporize cells near the cutting surface. Thus a cut is made with very little physical resistance to the cutting action. Heat from the cut cauterizes small blood vessels so that visibility and control remain good.

In the cautery mode and during uterine cavity distention, the same electrical resistance heating is used at lower power settings to cauterize tissue and to kill selected areas. Cautery electrodes can be larger in area so as to treat broader surfaces. Cautery is used in gynecology to ablate the endometrial lining of the uterus. This procedure is often performed using a conductive roller similar in shape to a football which heats a wide swath along the inner surface of the uterus.

Electrocautery tools are compact and require a minimum of area in which to work. Since the tool only cuts when the power is turned on, they can be safely maneuvered into small areas. Electrocautery has found broad general application in the treatment of enlarged prostate glands, and in the removal of uterine fibroids.

A secondary effect of the removal of tissue, particularly in the areas of prostate reduction and fibroid removal, is that severed morsels remain in the working area and must be periodically flushed or suctioned away to preserve the required visibility necessary for surgery. The clean, well controlled action of electrocautery is now slowed by the need to remove fragments which obstruct visibility. This required removal prolongs the surgical procedure.

It is known that ultrasound can add significant value to tissue resection and ablation procedures. Using high-frequency ultrasound, anatomical landmarks and tissue features can be imaged in depth, which cannot be done by optical instruments. Depth information provides improved guidance and monitoring capabilities. It enables the surgeon to monitor the progress of tissue treatment, and thereby lessens the risk of complications. In addition, the improved visualization provided by ultrasound can help to shorten procedure times.

At the present time as for example during uterine cavity distention, it is not practical to introduce ultrasound probes without considerable complication.

To perform ultrasound measurements during electrocautery, the surgical probes for the electrocautery procedure must first be removed and thereafter, ultrasound introduced. Finally, and after such measurements, surgery can resume with reintroduction of the surgical probes. With such procedures, the surgeon has difficulty returning to the original surgical site. For this reason, ultrasound is not usually utilized for measurement of uterine wall thickness by an intrauterine transducer.

SUMMARY OF THE INVENTION

A tissue resection device for preferred use in an organ inflated with substantially non-conductive optically transparent fluid under pressure is disclosed. The instrument includes a rigid shaft having a proximal end, a distal end, and defining a perfusion lumen extending therebetween. At the distal end of the shaft, the shaft is provided with a rounded blunt end having an elongate aperture exposing the lumen near the distal end. A removable drive tube is rotatably disposed within the shaft lumen and has a proximal end, a distal end, and a drive tube aspiration lumen extending therebetween. A cutting head is mounted on the distal end of the drive tube and has a laterally disposed cutting edge which can resect either by conventional cutting or electrocautery. This laterally disposed cutting edge is communicated to an internal passage between the cutting edge and the aspiration lumen of the drive tube so that tissue severed as the cutting head is rotated may be drawn directly into the aspiration lumen. A housing is attached to the proximal end of the shaft. Preferably, a DC motor in the housing is connected to rotate the drive tube and thus the laterally disposed cutting head. Connection is provided on the housing for connecting the perfusion shaft lumen to a perfusion source and the aspiration lumen to an aspiration source. Preferably, an optic fiber or hysteroscope at the proximal end of the elongate aperture of the shaft provides illumination and an optical view of surgery while a distally mounted and laterally exposed ultrasound transducer is disposed with a solid angle of interrogation including the surgical site. The surgical instrument finds preferred use in the uterus during uterine cavity distention where surgery occurs at the cutting head and can be disposable. During the surgical process, the cutting head is preferably drawn distally of the elongate cutting aperture towards the viewing optical fiber with the ultrasound transducer positioned to acoustically interrogate the operative site immediately after surgery.

A novel feature of this design is that the morsels removed by the cutter are extracted immediately through the aspiration lumen in the rotating shaft. Controlling the size of the chips, and directing them into the shaft center is achieved through the design of the cutter head. Controlled aspiration, typically by a finger actuated valve, occurs from within the cutter head to a retain sieve. Vision of the surgical site is improved.

Another novel feature of this design is a removable and disposable cartridge which surrounds the rotating cutter shaft where it enters the handle, and filters the surgical debris from the sorbitol-mannitol fluid used in the uterine cavity during the procedure for distention and visualization. The removed tissue is contained in the cartridge which can be sent intact to a laboratory for examination.

A feature of this design is that the handle, external shaft, and motor assembly can be re-used allowing for cost savings. The cutter head and shaft are intended to be disposable and can quickly plug into the handle assembly.

Another feature of this design is that a variety of cutter head configurations can be built which will allow for greater flexibility and effectiveness in treatments. A few examples are: an end-effect cutter for removing tissue at the end of the cutter axis; a smooth, or textured, head for ablation of uterine lining; and a narrow cutter for trimming the edge of a feature, or for cutting into a restricted area.

Another feature of this design is the control which is provided by the motorized operation. In conventional procedures, a surgeon is required to expend coordinated effort in moving and extracting debris in addition to actually making a series of cuts. With the motorized cutter and extraction system, the surgeon directs the cutter head to the area to be treated, and slowly draws the cutter through the fibroid to be removed. A trigger attached to the driving motor enables the cutting head to traverse the elongate aperture, preferably from the distal end to the proximal end toward the viewing fiber. Cutting is a matter of pressure and time at any particular area, and the feedback of the results is immediate through both visual observation and ultrasound interrogation in the wake of the resection. Fatigue is reduced, allowing for more precise work.

Another feature of this design is the ability to vary the motor speed and direction. Low speed cutting is more accurate and offers better control. Where a cutter head with electrocautery cutting edges is utilized, stopping or reversing the rotation offers the ability to treat the surface of an organ or to cauterize an area which is bleeding.

Another feature of this design is the use of the journal bearing as an electrical contact for the high voltage cutting current. This eliminates the need for a large slip-ring assembly, making the handle more compact and less expensive.

Yet another feature of this design is the mounting of the probe to a base unit adapted for fitting to the hand of the surgeon. Typically, the body of the drive unit is grasped between the hand and thumb. The forefinger (trigger finger) is utilized to cause the cutting head to traverse the elongate aperture for cutting at the surgical site. Motion of the housing directs the distal end of the probe to the surgical site.

Another feature of this design is the incorporation of the aspiration control valve into the handle. The valve is positioned so that it can be operated with one finger while steadying the tool and controlling the motion of the cutter with the rest of the hand. Aspiration can be made as vision and surgery requires with infusion through the instrument maintaining require cavity pressure.

Another feature of this design is that the cutter head and shaft, and scope can be removed from the outer sheath to allow the use of an obturator for dilating the cervix and introducing the sheath.

An added advantage of this invention is the incorporation of a sound transducer to the cutting head. Such a transducer can measure remaining organ wall thickness, preferably immediately after surgery. Surgery can be conveniently limited to avoid damage to adjacent organs.

BRIEF DESCRIPTION OF THE DRAWINGS

Other objects, features and advantages of this surgical instrument and accompanying procedure will become more apparent after referring to the following specification and attached drawings in which:

FIG. 7 is a detail of the probe at the point of attachment to the housing illustrating the disposition of the sieve for capture of the chips or morsels from surgery and illustrating how the disposable probe can be shipped (intact or bent) for compact shape for transport for biopsy of the retained chips or morsels; and, FIG. 8 is a section along lines 8–8 of FIG. 7 illustrating both the perfusion path and the aspiration path together with the relative locations of the probe, rotating tube, and path for the viewing optical fiber.

DESCRIPTION OF THE PREFERRED EMBODIMENT

Figure 1A:
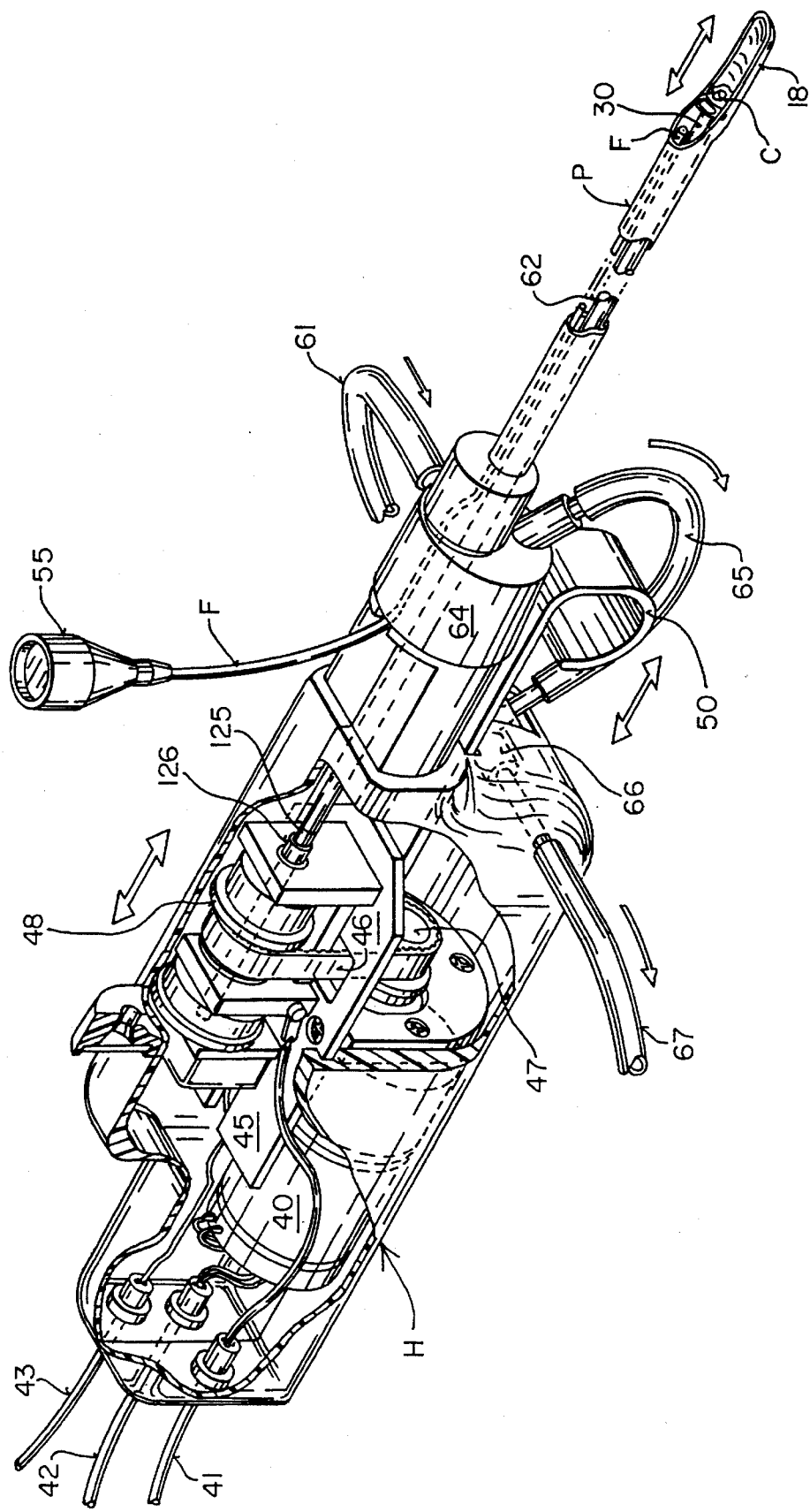
FIG. 1A is a perspective view of the drive housing with probe attached illustrating the housing and probe in partial section for understanding of the operative portions of the instrument.

Referring to FIG. 1A, surgical probe P is shown mounted to housing H. In understanding this invention, the probe P will first be discussed with respect to the preferred embodiment of FIG. 2A and 2B. Thereafter, the construction and operation of the probe from drive housing H in the hand of a surgeon will be discussed. Finally, alternate embodiments of the probe and cutting head as well as the capture of chips or morsels from the surgical site within the detachable probe will be set forth.

Figure 2A:
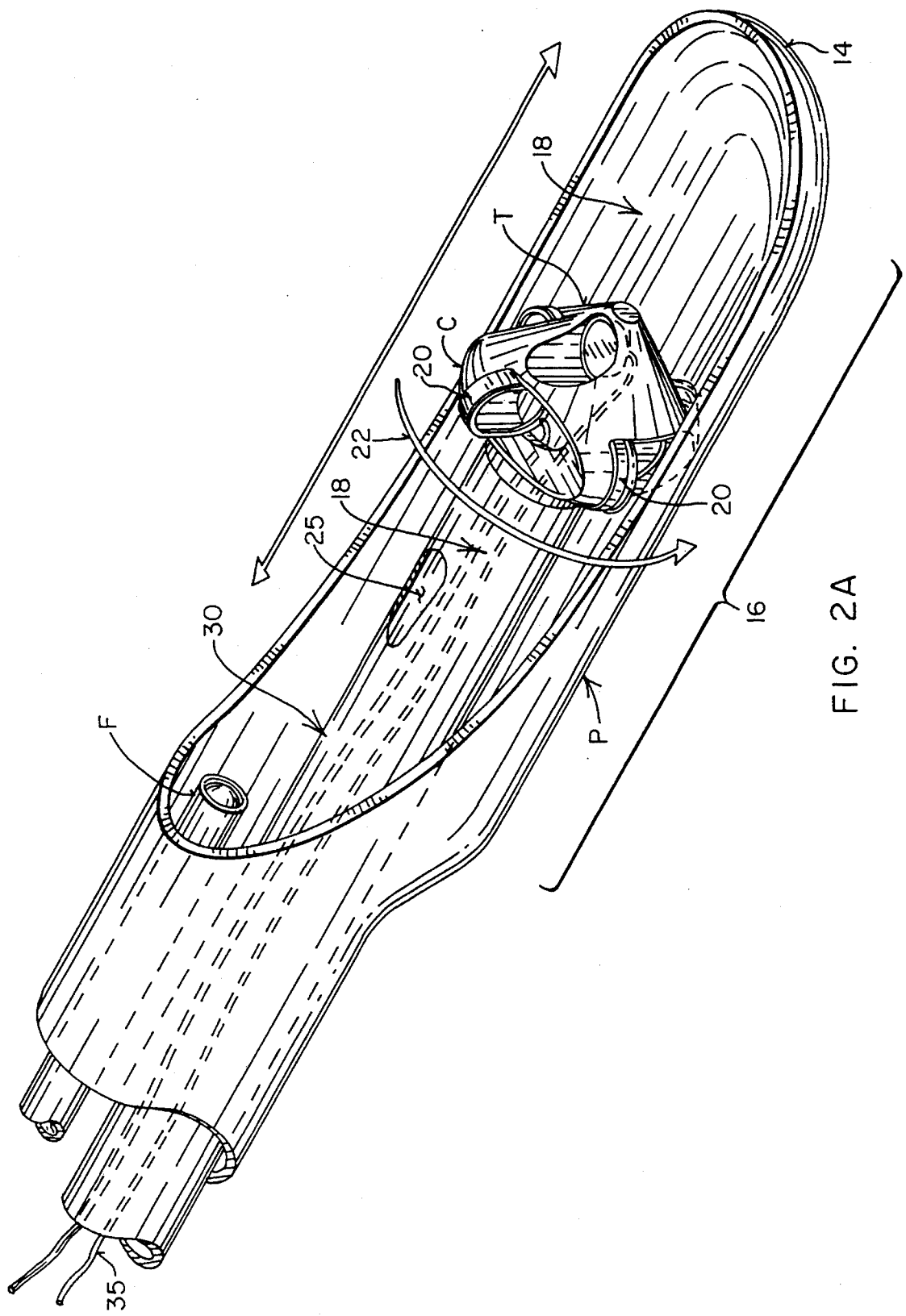
FIG. 2A is a section at the distal end of the probe illustrating the rigid shaft, elongate cutting aperture, infusion lumen, electrocautery cutting head, rotating cutting head driving tube with integral aspiration lumen, viewing optical fiber, and ultrasound transducer.
Figure 2B:
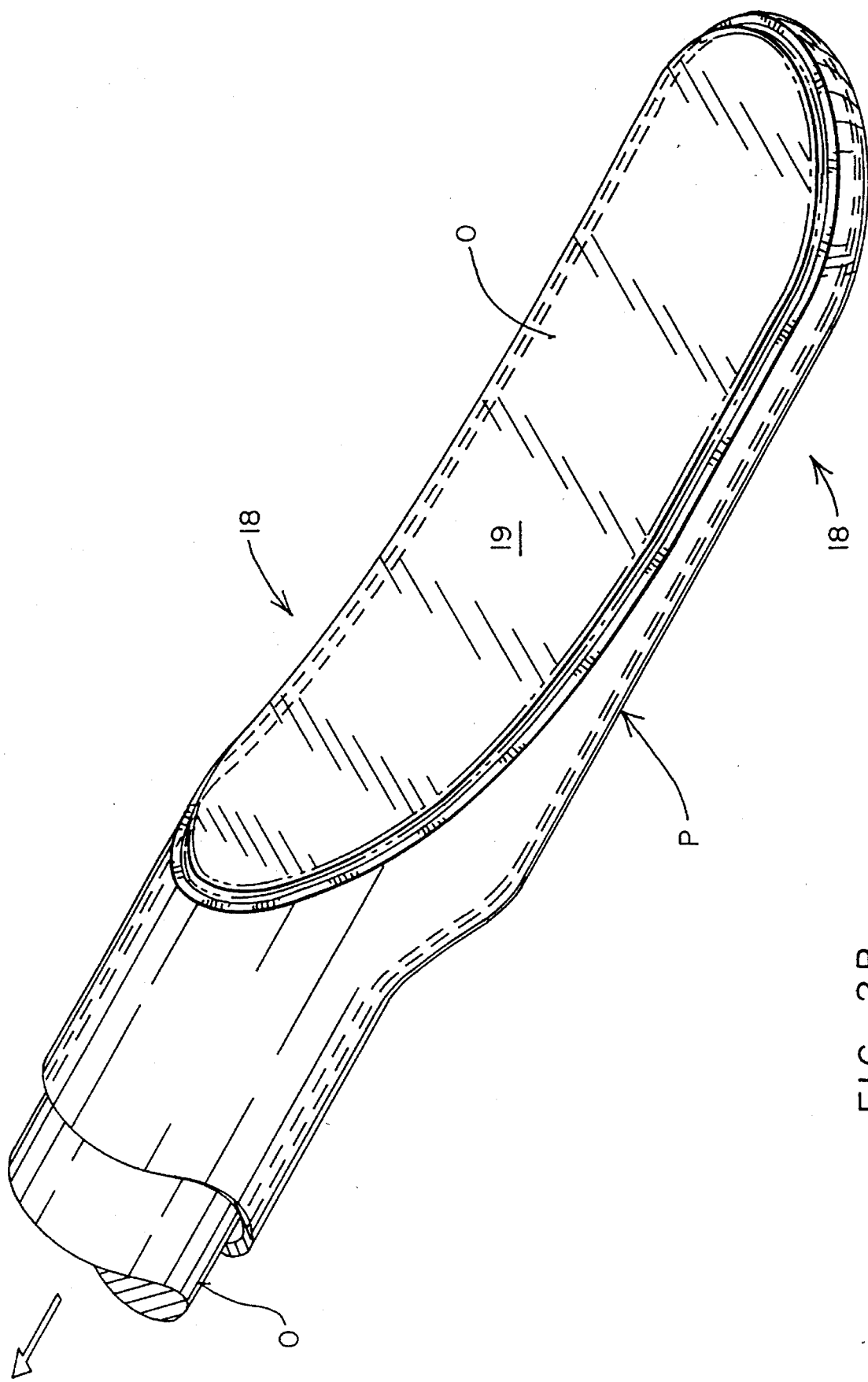
FIG. 2B is a perspective section similar to FIG. 2A with the cutting head removed, and an obturator in place for instrument insertion.

Referring to FIG. 2A and 2B, probe P is illustrated only at its distal and surgical end. Probe P is rigid having a blunted forward end 14 with an enlarged end 16 for fully accommodating the section of cutting head C. Exposure for surgery of cutting head C occurs at elongate slot 18 with view of the cutting head C during surgery within slot 18 being provided by optical fiber F at the proximal end of the slot. In FIG. 2B, probe P is disclosed occupied by obturator O. It is in this mode that probe P is inserted.

An electrocautery cutting head C is provided. Head C includes electrically conductive cutting edges 20 which are radially exposed from the cutting head C for surgical resection when head C is rotated in the direction of arrow 22. Head C is hollow and communicates to rotating driving tube 30 with interior aspiration lumen 25. An ultrasound transducer T rotates with cutting head C and sends and receives acoustical signals through wire 35. This transducer can measure remaining uterine wall thickness immediately after surgery when head C is in elongate slot 18 drawn proximally or distally of elongate slot 18 or at any intermediate position with respect to the slot.

Cautery alone utilizing probe P can occur. Specifically, by rotating cutting head C opposite to arrow 22, electrocautery cutting heads 20 pass in a blunted and non incisive path over the flesh. Cautery results.

Having generally discussed the construction of the probe, attention can now be directed to handle H.

Referring to FIG. 1A, handle H includes DC motor 40 electrical connections 42—it being recognized that reversal in motor polarity causes reversal in motor direction. Electrocautery connection is routed via a standard cautery power supply through conduit 41 to a journal bearing connection (see FIG. 1A Accoustical transducer T (seen in FIG. 2A) at cutting head C sends and receives electrical signals through lead 43. A conventional slip coupling—not shown—is provided to wire 35 in tube 30 to lead 43.

Motor 40 is mounted to plate 45 and provides driving rotation at toothed pulley 47. Belt 46 drives toothed pulley 48 which in turn rotates drive tube 30 through quick disconnect coupling 125. This quick disconnect coupling is the point of removable attachment of the probe. (See FIG. 7)

Drive tube 30 is of constant length. Forefinger trigger 50 attaches directly to plate 45 which is mounted for sliding translation interior of handle H. By movement of trigger 50 relative to housing H, corresponding movement of cutting head C occurs along elongate slot 18. Video camera coupler 55 communicates to fiber F having illumination strands for viewing of the applicable surgery.

Referring to FIG. 1A, the fluid circuit for maintaining uterine cavity distension is only illustrated in pertinent part It is presumed that standard technology will be used to maintain required pressure for uterine cavity distension through inlet conduit 61. Inlet conduit 61 communicates to probe P in the infusion lumen 62. By maintaining a constant pressure sufficient to establish uterine distention, required inflation is maintained in the organ—here the uterus—in which the operation occurs.

Referring to FIG. 7, fluid exits the site of the surgery through lumen 25 in rotating tube 30 and passes to chamber 130 where chips or morsels from surgery are captured. Thereafter, aspirated fluid passes through conduit 65 to finger actuated valve 66 and thence to state of the art fluid capture apparatus. As is customary in such procedures, chips or morsels are routed to pathology for investigation including biopsies where required. The instrument may be shipped intact or be bent (as at shaft 30) for convenience. Disposal can thereafter occur.

Figure 1B:
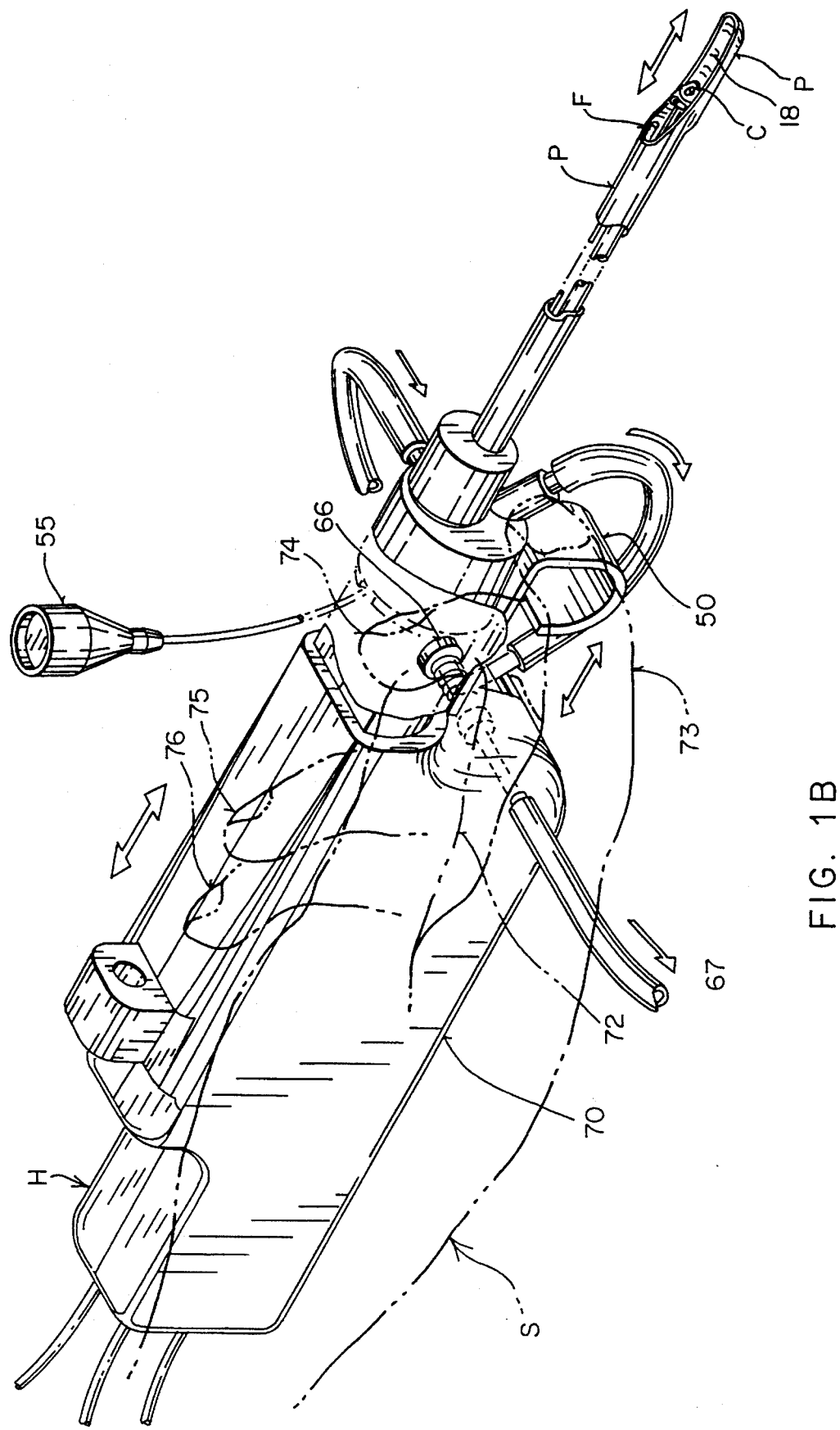
Fig. 1B is a perspective of the drive housing H with probe attached illustrating the housing grasped in the hand of the surgeon (shown in broken lines) demonstrating the surgical instrument manipulation of the rigid probe to dispose the elongate aperture at the surgical site, trigger finger manipulation of the cutting head relative to the viewing fiber and ultrasound transducer, and finger actuated aspiration during surgery.

Referring to FIG. 1B, the surgical ergonomics of housing H can be appreciated. Taking the case of a right handed surgeon, housing H at bottom surface 70 is held by hand S with thumb 72 opposing the third, forth and fifth fingers 74, 75 and 76. Forefinger 73 grips trigger 50 and by movement of finger 73 relative to housing H causes inward and outward traverse of cutting head C relative to elongate slot 18 of probe P. Middle finger 74 depresses valve 66 to cause applicable aspiration for example when view from eyepiece 55 indicates obstruction. Thus, flushing of sorbitol-mannitol solution distending the uterus can occur at intermittent and successive intervals as required by the surgical procedure.

Figures 3A, 3B:
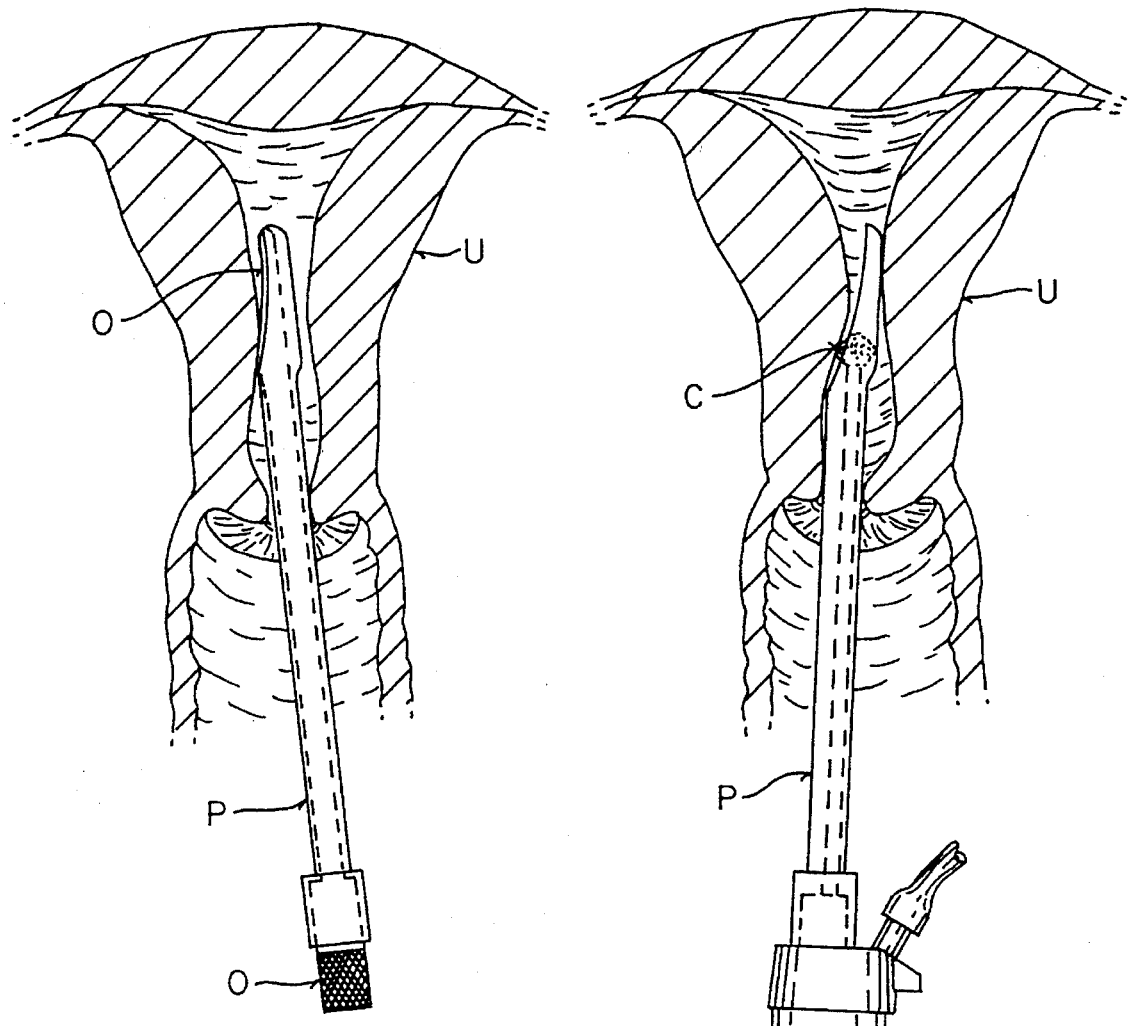
FIG. 3A, 3B and 3C are respective sections of a uterus respectively illustrating the probe with an obturator during insertion for surgery, the instrument with rotating shaft and cutting head being inserted to the probe; and the insertion of the optical fiber for completion of the the assembled probe.
Figure 3C:
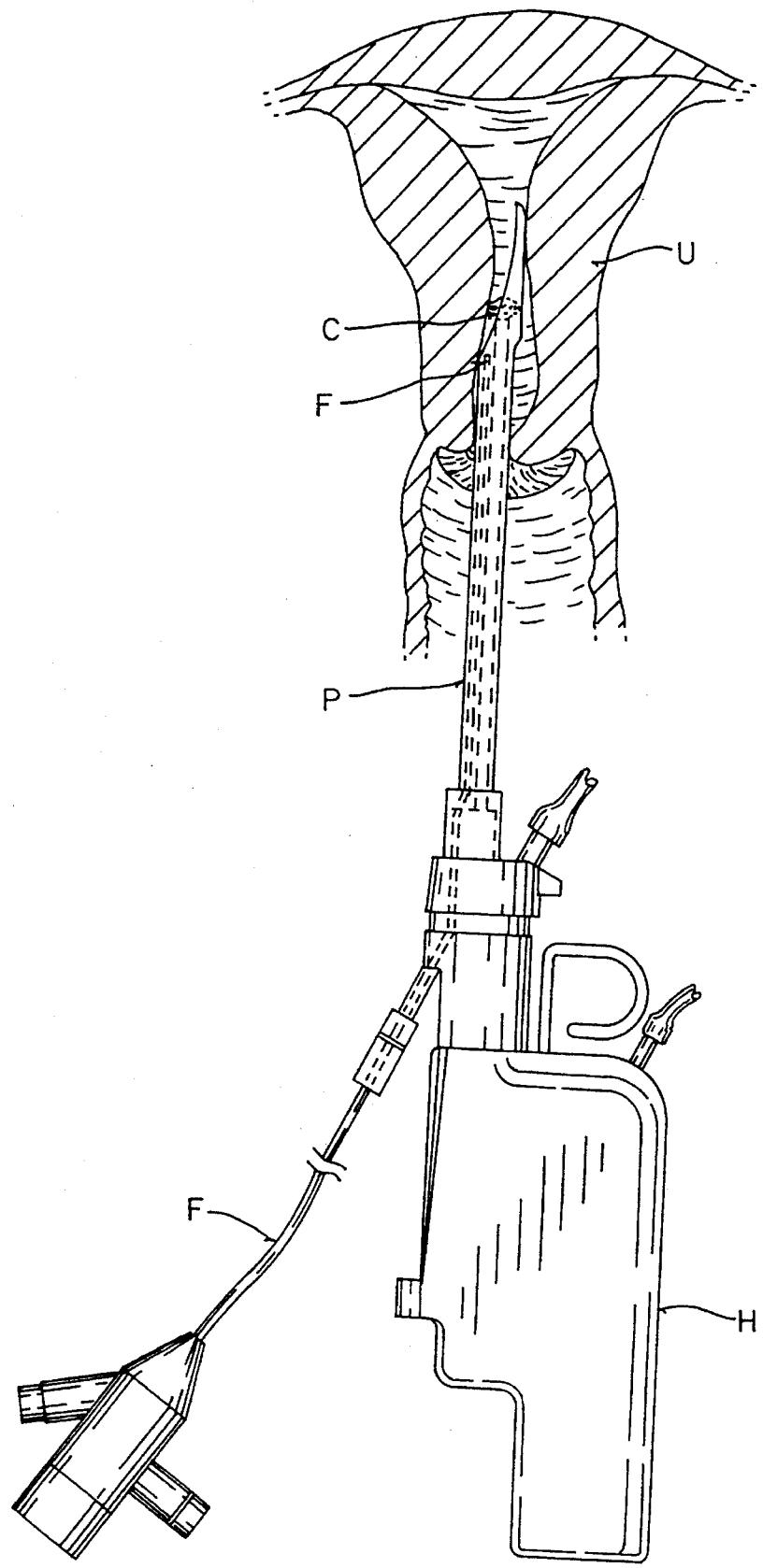

Insert of the instrument is easy to understand. Referring to FIG. 3A, probe P with obturator O is inserted uterus U. Thereafter, obturator O is withdrawn, and housing H with cutting head C threaded (See FIG. 3B). Once this insertion is made, fiber F is thereafter inserted for visualization of the surgical site (See FIG. 3C and the section of FIG. 8). Operative movement of the instrument can thereafter occur as illustrated in FIG. 4.

Figure 4:
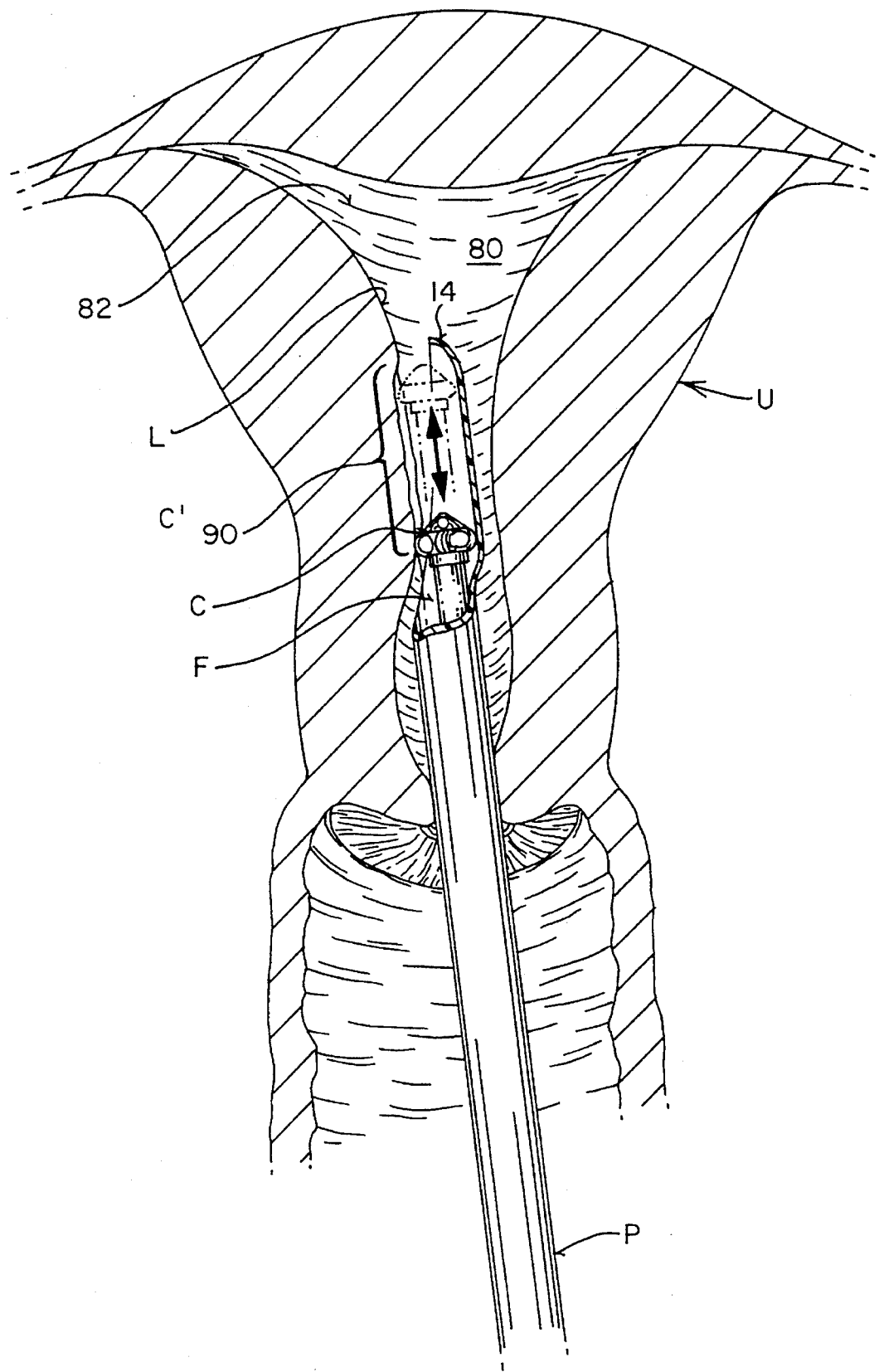
FIG. 4 is a section similar to the sections of FIGS. 3A–3C illustrating the working end of the instrument at an operative site.

The instrument in use can be visualized in the uterine section of FIG. 4. Probe P is shown with blunt end 14 within uterine cavity 80. This cavity is flooded with sorbitol-mannitol solution 82 so as to dispose lining L for surgery. In the preferred method, cutting head C is disposed at C". Under the guidance of fiber F, probe P is maneuvered to surgical site. Assuming resection, cutter head C is drawn proximally of elongate slot 18 in probe P. With the preferred construction illustrated in FIG. 4, three occurrences follow.

First, and starting with cutting head C distally of elongate slot 18, view of the tissue before resection is provided. Secondly, and with traverse of cutting head C, surgical resection occurs. Thirdly, and immediately in the wake of the required resection, acoustical transducer T interrogates uterus U immediately after the surgery.

It will be remembered that evacuation of fluid occurs directly from the cutting edges of cutting head C to rotating tube 30 with its aspiration lumen 25. Accordingly, flushing of chips and morsels is immediate the surgical site 90 with minimal chance for clouding the required view through fiber F.

Figure 5:
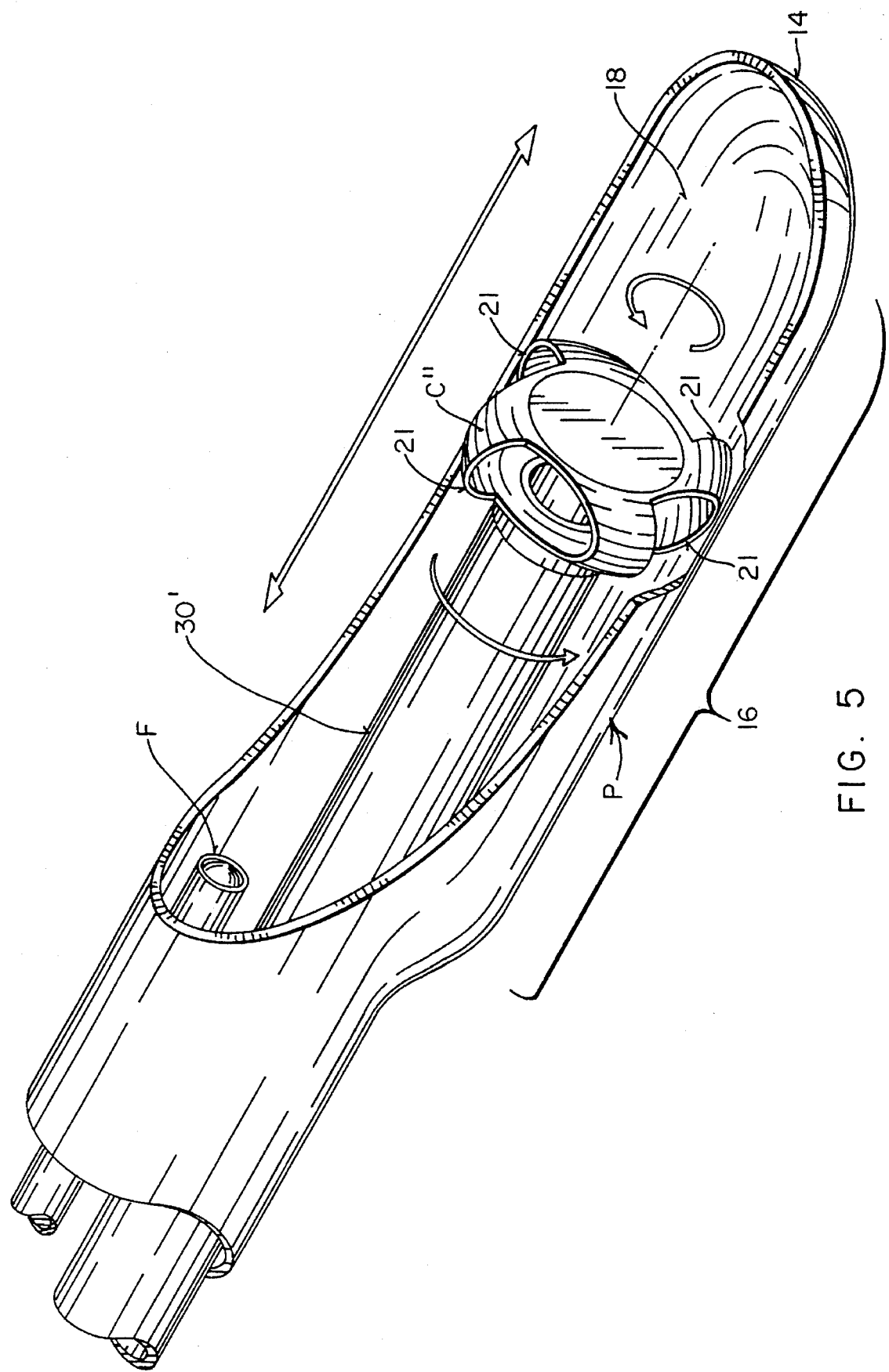
FIG. 5 is a section similar to FIG. 2A of an alternate embodiment of the probe here illustrated with a conventional cutting head without ultrasound interrogation.

Referring to FIG. 5, an alternate embodiment of cutting head C" is illustrated. Cutting head C" is hollow, attached to rotating tube 30', and included semi-spherical cutting edges 21. It will be noted that this head does not include acoustical transducer T nor does it include electrocautery. While both these features are preferred, they are not required.

It is to be understood that acoustical interrogation of uterus U immediately after surgery is not trivial. Specifically, and during the illustrated procedure utilizing operating tools and procedures of the prior art, one of the most difficult assignments of the surgeon is not to cut entirely through the uterus. Such cutting causes morbidity such as iatrogenic uterine perforation and can damage nearby body structures such as bowel.

Fortunately, soft tissue organs such as uterus U can be acoustically interrogated for their remaining wall thickness after resection. Thus transducer T can output through conventional acoustical visualizing apparatus the thickness remaining of the organ. Additionally, and with a conventional shaft encoder, an acoustical section or well known "B" scan of the section at the angle of view of the transducer can be displayed. For example, the remaining width when below a predetermined thickness can be utilized with its telltale acoustical signal to trigger an alarm warning the surgeon when remaining thickness is below a set tolerance.

Figure 6B:
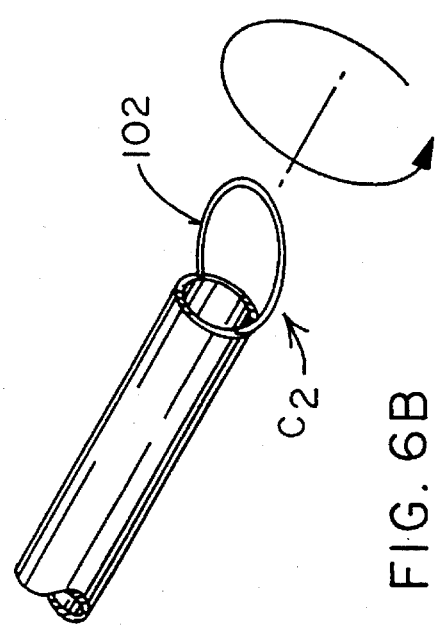
FIGS. 6A–6C are differing cutting heads utilized with this instrument.
Figure 6A:
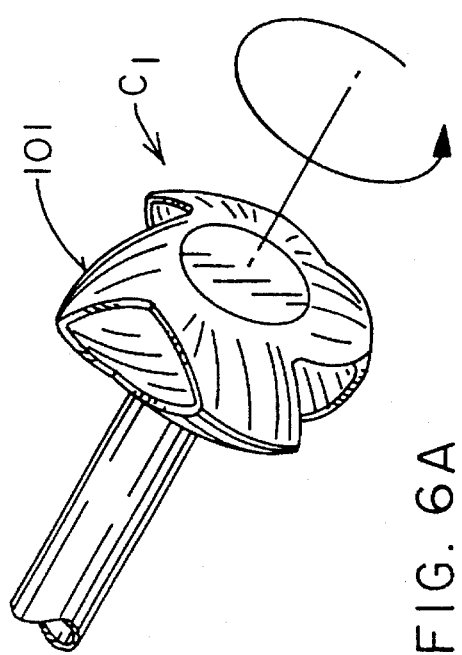
Figure 6C:
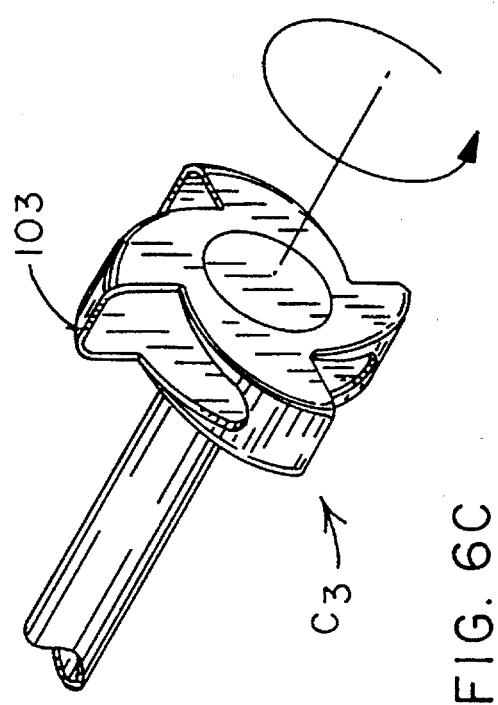

It will be apparent that the tool of this application will admit of a number of differing cutting heads. For example, as indicated in FIG. 6A, it may be desired to have the cutting head end in a V-shaped cutting profile 101. Further and as set forth in FIG. 6B, and with modification to the probe, a rotating U-shape cutter 102 may be required for distal or end-on access to surgical sites. Finally, and as set forth in FIG. 6C, a flat cutter 103 is shown. It will be realized that this invention will admit of other shapes. Further, the respective cutting heads can either be conventional knives or be provided with suitable paths for electrocautery.

Referring to FIG. 7, the aspiration of fluid from the surgical site together with the trapping of morsels from surgery from the aspirated fluid can be understood. First, perfusion fluid is introduced through conduit 61 into perfusion chamber 100. It then enters probe P.

Viewing FIG. 8 at this juncture can be instructive. Specifically, bearing member 102 with fiber F and rotating tube 30 receiving concavities is placed interior of probe P and extends almost the full length of the lumen within probe P. It includes a lower round aperture 107 which is the surface against which rotating shaft 30 bears. The upper surface forms a saddle which locates and guides the viewing scope F which may be flexible. The remaining interior volume of probe P forms a channel which contains the perfusion fluid. Exit of the fluid occurs through slot 18 and the end of probe P.

Rotating shaft 30 extends completely through chamber 100 and into and through a housing defining chamber 130. Chambers 100 and 130 may be separated by an O-ring (See FIG. 7) or other suitable seal. It is in this housing that the morsels from surgery are trapped. Thereafter, shaft 30 terminates at a quick disconnect coupling 125 which couples to a counter part coupling member 126 driven by motor 40. (See FIG. 1B for this detail).

Interior of chamber 130, shaft 30 is provided with an aperture 128. Aperture 128 allows aspirated fluid to be communicated to chamber 130. Aspirated fluid is withdrawn from chamber 130 through conduit 65. Conduit 65 communicates through valve 66 and outflow conduit 67 for the discharge of aspirated fluid. (See FIG. 1B for valve 6 and conduit 67)

Screen 135 divides chamber 130 between aperture 128 (which rotates with shaft 30) and conduit 65. As a consequence, morsels from surgery are trapped on screen 135. This being the case, the attached probe P when removed from handle H can constitute both a disposable appliance as well as a convenient cartridge 64 for transport of surgical morsels for biopsy. (See FIG. 1A and 7)

As is apparent, the disposable portion of the device may or may not include probe P.

As a known alternative to the cautery illustrated herein, heated fluids can be flowed through the instrument to coagulate the tissue.

The preferred and illustrated application of this design is for trans-cervical fibroid removal, removal of myometrium, and removal of endometrium. Other uses of instruments substantially incorporating this design are listed below:

Intrauterine (Hysteroscopy)
    Uterine wall Resection
    Endometrial Ablation
    Endometrial Resection
    Submucous Myoma Resection
    Intramural Myoma Resection
    Transmural Myoma Resection
    Resection of Cervix and Cervical Canal
Kidney Resection (Laparoscopy)
    Retroperitoneal
Prostate Resection (Cystoscopy)
Intra-abdominal (Laparoscopy)
    Uterine Myomectomy
    Ovary Resection
Lung tissue and Tumors (Thoracoscopy)
Measuring Device (Ultrasonic Transducer)
    Uterine Wall Thickness
    Endometrium Thickness
    Prostate Thickness
    Intra uterine measurements
    Urethra thickness The above procedures may require relatively minor modifications of the disclosed device.

What is claimed is:

1. A tissue resection device comprising:

a shaft having a proximal end, a distal end, a lumen extending therebetween, and an elongate aperture exposing the lumen neat the distal end;

a drive member comprising a tube, said drive member rotatably disposed within the shaft lumen and having a proximal end, and a distal end;

a cutting head mounted on the distal end of the drive member and having a laterally disposed cutting edge;

a housing attached to the proximal end of the member;

means in the housing connected to rotate the drive member;

means on the housing for routing through the shaft lumen a perfusion source and an aspiration outlet;

an ultrasonic imaging transducer on said device for ultrasonically imaging tissue at a surgical site to determine depth of tissue to be resected:

wherein a perfusion lumen is within said probe said probe; and, an aspiration lumen is within said tube.

2. A device as in claim 1, further comprising a fiber optic attached to the shaft and having a viewing end disposed adjacent the cutting head, whereby cutting of tissue using the head may be observed.

3. A device as in claim 1, wherein the ultrasonic transducer is mounted on the cutting head, whereby the tissue to be resected can be ultrasonically imaged.

4. A device as in claim 1, further comprising means on the housing for connecting the cutting head to an electrosurgical power supply.

5. A device as in claim 1, further comprising means for axially reciprocating the drive member so that the cutting head may be moved back and forth across the elongate aperture as the cutting head is rotated.

6. A device as in claim 5, wherein the axially reciprocating means comprises a carriage supporting the motor and a linkage between the motor and the drive member.

7. A device as in claim 1, further comprising a collection trap at the proximal end of said probe for separating resected tissue from the perfusion fluid as it is being aspirated.

8. The device of claim 1, further comprising a cutting guard at the distal end of the shaft and opposite the elongate aperture.

9. A probe for surgery of a perfused surgical site comprising in combination:

a shaft having a proximal end, a distal end, a lumen extending therebetween, and an elongate aperture extending adjacent the distal end of said probe for exposing the lumen near the distal end;

a drive tube rotatably disposed within the shaft lumen and having a proximal end, a distal end, and an aspiration lumen extending therebetween;

a cutting head mounted on the distal end of the drive tube and having a laterally disposed cutting edge relative to an axis along the lumen of the tube and an internal passage between the cutting edge and the aspiration lumen of the drive tube, the cutting head having means for directing tissue resected by the laterally disposed cutting edge into the aspiration lumen for withdrawal from the surgical site; and wherein said exposed cutting edges are provided with a conductive path to said edges for electrocautery.

10. The probe of claim 9 and wherein said cutting head includes exposed cutting edges for contacting said tissue upon rotation of said head.

11. The probe of claim 9 and wherein said cutting head includes an ultrasound imaging transducer for determining depth of tissue to be resected.

12. The probe of claim 9 and including means for gathering morsels connected to said aspirating lumen.

13. The probe of claim 9 and including an optical fiber disposed in said tube for view of said elongate aperture.

14. A tissue resection device comprising:

a shaft having a proximal end, a distal end, a lumen extending therebetween, and an elongate aperture exposing the lumen near the distal end;

a drive member rotatably disposed within the shaft lumen and having a proximal end, and a distal end;

a cutting head mounted on the distal end of the drive member and having a laterally disposed cutting edge;

a housing attached for the proximal end of the member;

means in the housing connected to rotate the drive member;

means on the housing for routing through the shaft lumen a perfusion source and an aspiration outlet;

an ultrasonic imaging transducer on said device for ultrasonically imaging tissue at a surgical site to determine depth of tissue to be resected; and a fiber optic attached to the shaft and having a viewing end disposed adjacent the cutting head, whereby cutting of tissue using the head may be observed.

15. A tissue resection device comprising:

a shaft having a proximal end, a distal end, a lumen extending therebetween, and an elongate aperture exposing the lumen near the distal end;

a drive member rotatably disposed within the shaft lumen and having a proximal end, and a distal end;

a cutting head mounted on the distal end of the drive member and having a laterally disposed cutting edge;

a housing attached to the proximal end of the member;

means in the housing connected to rotate the drive member;

means on the housing for routing through the shaft lumen a perfusion source and an aspiration outlet;

an ultrasonic imaging transducer on said device for ultrasonically imaging tissue at a surgical site to determine depth of tissue to be resected; and means on the housing for connecting the cutting head to an electrosurgical power supply.

16. A device as in claim 15, wherein the cutting edge of the cutting head is electrically conductive so that electrosurgical cutting can be effected.

17. A device as in claim 15, wherein non-cutting portions of the cutting head are electrically conductive so that electrocautery can be effected while the head is rotating or not rotating.

18. The device of claim 15, further comprising a wire for electrically coupling the power system to the cutting edge.

19. A tissue resection device comprising:

a shaft having a proximal end, a distal end, a lumen extending therebetween, and an elongate aperture exposing the lumen near the distal end;

a drive member rotatably disposed within the shaft lumen and having a proximal end, and a distal end;

a cutting head mounted on the distal end of the drive member and having a laterally disposed cutting edge;

a housing attached to the proximal end of the member;

means in the housing connected to rotate the drive member;

means on the housing for routing through the shaft lumen a perfusion source and an aspiration outlet;

an ultrasonic imaging transducer on said device for ultrasonically imaging tissue at a surgical site to determine depth of tissue to be resect; and further comprising a collection trap at the proximal end of said probe for separating resected tissue from the perfusion fluid as it is being aspirated.

20. A device as in claim 19, wherein the collection trap includes:

a chamber having said rotating member passing therethrough, said rotating member including a lumen proximate said cutting head;

an aperture in said rotating member at said chamber;

a chamber outlet; and, a screen having a mesh size for dividing said chamber between said aperture on said evacuation port and said chamber outlet.

21. A probe for surgery of a perfused surgical site comprising in combination:

a shaft having a proximal end, a distal end, a lumen extending therebetween, and an elongate aperture extending adjacent the distal end of said probe for exposing the lumen near the distal end;

a drive tube rotatably disposed within the shaft lumen and having a proximal end, a distal end, and an aspiration lumen extending therebetween;

a cutting head mounted on the distal end of the drive tube and having a laterally disposed cutting edge relative to an axis along the lumen of the tube and an internal passage between the cutting edge and the aspiration lumen of the drive tube, the cutting head having means for directing tissue resected by the laterally disposed cutting edge into the aspiration lumen for withdrawal from the surgical site; and wherein said drive tube is moveable for transit along said elongate slot for enabling said cutting head to resect tissue exposed to said probe at said aperture.

22. A probe for surgery of a perfused surgical site comprising in combination:

a shaft having a proximal end, a distal end, a lumen extending therebetween, and an elongate aperture extending adjacent the distal end of said probe for exposing the lumen near the distal end;

a drive tube rotatably disposed within the shaft lumen and having a proximal end, a distal end, and an aspiration lumen extending therebetween;

a cutting head mounted on the distal end of the drive tube and having a laterally disposed cutting edge relative to an axis along the lumen of the tube and an internal passage between the cutting edge and the aspiration lumen of the drive tube, the cutting head having means for directing tissue resected by the laterally disposed cutting edge into the aspiration lumen for withdrawal from the surgical site; and means for continuous perfusion and aspiration of the surgical site.

23. A method for resetting tissue, said method comprising:

providing a probe defining a lumen and having a distal end open at an elongate slot;

providing a rotatable cutting head having laterally disposed cutting edges relative to an axis along the lumen of the probe, the cutting head having a dimension sufficient to fit into and through said lumen of said probe, said cutting head having means for directing tissue resected by said cutting edges into said lumen;

providing a tube attached to said rotatable cutting head so that said cutting head is disposed at said elongate aperture;

inserting said probe with said elongate slot confronted to a surgical site;

rotating the tube to rotate said cutting head in contact with tissue to be resected;

perfusing the surgical site with perfusion fluid and aspirating the surgical site through said lumen to draw resected tissue from said surgical site; and applying radio frequency energy to the cutting head as it is rotated at a frequency selected to enhance cutting.

24. A method as in claim 23, including the step of applying radio frequency energy to the cutting head at a frequency selected to enhance coagulation.

25. A method as in claim 23, including the steps of reversing the rotation of the cutting head while the radio frequency energy is applied to cauterize with said cutting head.

26. A method as in claim 23, further comprising optically viewing the tissue to be resected while contacting with the cutting head.

27. A method as in claim 23, further comprising providing a sounds transducer on said cutting head; and, ultrasonically viewing the tissue through said sound transducer to determine depth of tissue to be resected.

28. A method as in claim 23, further comprising the steps of:

aspirating a perfusion fluid from said surgical site through a tube attached to said cutting head.

29. A method as in claim 23, including the steps of:

perfusing said surgical site through said probe.

30. A method of inserting for surgery a resectoscope for operating on tissue at a surgical site in a perfused cavity interior of a human comprising the steps of:

providing a probe having a distal and proximal end and defining a lumen therebetween, said distal end of said probe including an elongate slot adjacent a blunt end;

providing an obturator for occupying said probe at said slot for enabling insertion of said probe to said cavity in said human;

placing said obturator in said probe from said proximal end to occupy said elongate slot and inserting said probe to said cavity in said human body;

withdrawing said obturator from said probe through the proximal end of said inserted probe;

perfusing said cavity with fluid through said lumen in said probe;

providing a rotatable member having a cutting head mounted on the distal end thereof and a proximal end adapted to be rotated, said cutting head and rotating member having a dimension less than the lumen of said probe;

inserting said cutting head and said rotating member to said lumen at said proximal end of said probe to protrude said cutting head from said probe at said slot at said distal end of said probe;

providing an optical fiber for visualizing said cutting head;

inserting said fiber along said lumen to visualize said cutting head in said probe at said slot at said distal end of said probe; and, rotating said cutting head from said rotatable member at the distal end of said probe during said visualization for operating at said surgical site.

31. A method of inserting for surgery a resectoscope according to claim 30 further comprising:

providing a lumen in said rotatable member between the distal end of said member adjacent said cutting head and the proximal end of said member; and, aspirating said perfused surgical site through said lumen in said rotatable member.

32. A method of inserting for surgery a resectoscope according to claim 30 further comprising:

perfusing said cavity with a substantially non-conductive fluid;

providing an electrical path in said rotatable member to said cutting head; and, supplying electrical energy sufficient for cautery to said cutting head.

33. A method of inserting for surgery a resectoscope according to claim 30 and further including:

providing an acoustical transducer in said cutting head having sufficient dimension to fit within said lumen of said probe from said proximal end to said distal end; and, sending and receiving sound at said acoustical transducer during said rotation of said cutting head for acoustical examination of said surgical site.

34. A method for resecting tissue from the uterus, the method comprising:

removing tissue from the uterus by applying a cutter or radio frequency to the tissue;

viewing depth of tissue resection in the uterus while removing the tissue; and evacuating the removed tissue from the uterus.

35. A method for resecting tissue, said method comprising:

providing a probe defining a lumen and having a distal end open at an elongate slot;

providing a rotatable cutting head having laterally disposed cutting edges relative to an axis along the lumen of the probe, the cutting head having a dimension sufficient to fit into and through said lumen of said probe, said cutting head having means for directing tissue resected by said cutting edges into said lumen;

providing a tube attached to said rotatable cutting head so that said cutting head is disposed at said elongate aperture;

inserting said probe with said elongate slot confronted to a surgical site;

rotating the tube to rotate said cutting head in contact with tissue to be resected;

perfusing the surgical mite with perfusion fluid and aspirating the surgical site through said lumen to draw resected tissue from said surgical site; and applying radio frequency energy to the cutting head at a frequency selected to enhance coagulation.

36. A method for resecting tissue, said method comprising:

providing a probe defining a lumen and having a distal end open at an elongate slot;

providing a rotatable cutting head having laterally disposed cutting edges relative to an axis along the lumen of the probe, the cutting head having a dimension sufficient to fit into and through said 1omen of said probe, said cutting head having means for directing tissue resected by said cutting edges into said lumen;

providing a tube attached to said rotatable cutting head so that said cutting head is disposed at said elongate aperture;

inserting said probe with said elongate slot confronted to a surgical site;

rotating the tube to rotate said cutting head in contact with tissue to be resected;

perfusing the surgical site with perfusion fluid and aspirating the surgical site through said lumen to draw resected tissue from said surgical site; and optically viewing the tissue to be resected while contacting with the cutting head.

* * * * *